United States Patent [19]

Rescigno

[11] Patent Number: 4,884,581
[45] Date of Patent: Dec. 5, 1989

[54] ORAL HYGIENE TONGUE HOLDER

[76] Inventor: Josephine Rescigno, 918 N. Beverly Dr., Beverly Hills, Calif. 90210

[21] Appl. No.: 218,446

[22] Filed: Jul. 12, 1988

Related U.S. Application Data

[63] Continuation of Ser. No. 894,086, Aug. 7, 1986, abandoned, which is a continuation of Ser. No. 800,352, Nov. 20, 1985, abandoned, which is a continuation of Ser. No. 708,113, May 5, 1985, abandoned, which is a continuation of Ser. No. 357,198, Mar. 11, 1982, abandoned.

[51] Int. Cl.$^4$ .......................... A01F 13/00; A01F 5/56; A01F 5/58
[52] U.S. Cl. ..................... 128/869; 433/140; 433/111; 433/153; 15/110; 15/111; 15/167.1
[58] Field of Search ............... 128/133, 136, 137, 12, 128/15, 321, 346, 357, 777, 848, 860, 867; 433/140, 141, 153, 157; 401/130, 132; 15/104.94, 227, 159 R, 160, 167.1, 110, 111; 81/43; 2/21

[56] References Cited

U.S. PATENT DOCUMENTS

| D 157,104 | 1/1950 | Tuttle et al. | 128/354 |
|---|---|---|---|
| 625,879 | 5/1899 | Gardner | 128/137 |
| 888,991 | 5/1908 | Fulton | 2/21 |
| 1,235,199 | 7/1917 | Gavin | 2/21 |
| 1,306,442 | 6/1919 | Sansotta | 2/21 |
| 1,405,689 | 2/1922 | Heatwole | 728/860 |
| 1,483,595 | 2/1924 | Read | 2/21 |
| 1,891,864 | 12/1932 | Barrett | 15/111 |
| 1,947,720 | 2/1934 | Laub | 15/227 |
| 2,039,505 | 5/1936 | Vollmer | 2/21 |
| 2,041,262 | 5/1936 | Ness | 15/227 |
| 2,064,986 | 12/1936 | Mezz | 128/132 R |
| 2,092,987 | 9/1937 | Remington | 15/227 |
| 2,101,363 | 12/1937 | De Rome | 15/227 |
| 2,112,189 | 3/1938 | Vogan | 15/227 |
| 2,232,396 | 2/1941 | Lee, et al. | 2/21 |
| 2,467,613 | 4/1949 | Davis | 2/21 |
| 2,751,592 | 6/1956 | Lonstreth, et al. | 2/21 |
| 2,966,911 | 1/1961 | Cameron | 15/227 |
| 3,263,681 | 8/1966 | Nechtow, et al. | 128/157 |
| 3,293,958 | 12/1966 | Smith | 81/43 |
| 3,513,835 | 5/1970 | Ceuster | 128/12 |
| 3,735,426 | 5/1973 | Horvath | 81/43 |
| 3,798,698 | 3/1974 | Conklin, Jr. | 15/227 |
| 3,809,094 | 5/1974 | Cook | 128/321 |
| 3,862,507 | 1/1975 | Martyn | 81/43 |
| 4,198,967 | 4/1980 | Dror | 128/136 |
| 4,335,731 | 6/1982 | Bora, Jr. | 15/227 |
| 4,617,694 | 10/1986 | Bori | 15/160 |
| 4,620,528 | 11/1986 | Arraval | 15/227 |

FOREIGN PATENT DOCUMENTS

| 81221 | 12/1919 | Fed. Rep. of Germany | 128/346 |
|---|---|---|---|
| 679941 | 7/1939 | Fed. Rep. of Germany | 128/346 |
| 0119217 | 9/1921 | United Kingdom | 15/167.1 |

Primary Examiner—Max Hindenburg
Assistant Examiner—K. M. Reichle
Attorney, Agent, or Firm—Wigman & Cohen

[57] ABSTRACT

It is often necessary to manipulate or extend a tongue in order to perform an operation on the tongue or inside the mouth. The apparatus and method claimed provide non-slip surfaces which are attached to a user's finger and thumb, and which are maintained in an optimal predetermined physical relationship to each other so that the apparatus may be easily attached to the user's finger and thumb, and so that a positive and comfortable contact with the tongue is achieved. Thereby, the tongue may be manipulated or restrained in any position, even fully extended.

17 Claims, 1 Drawing Sheet

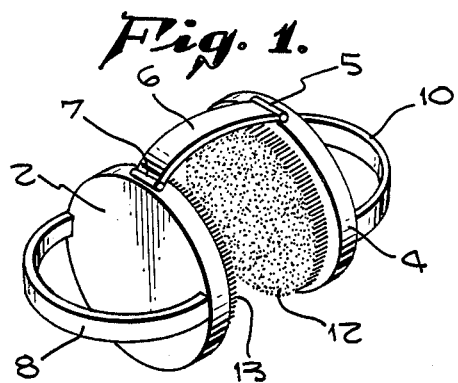
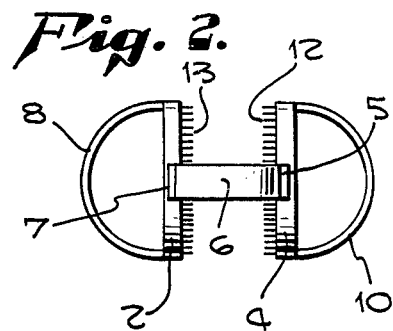
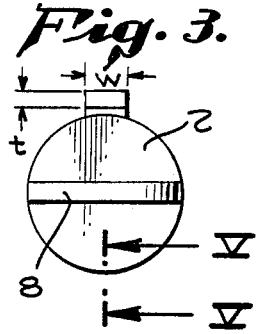
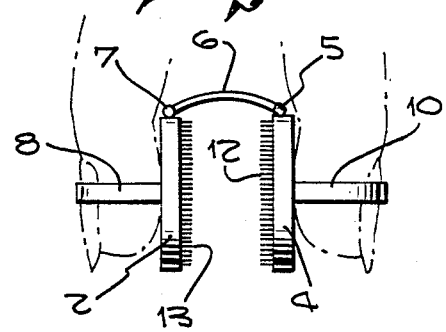
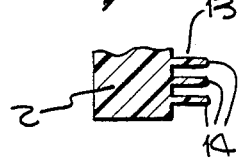
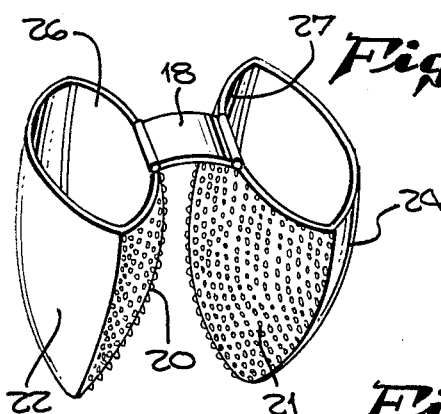
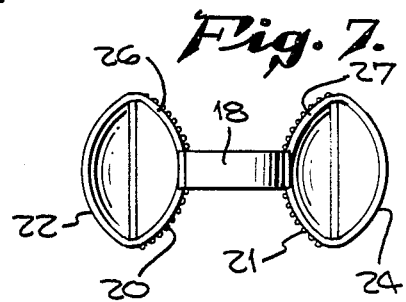
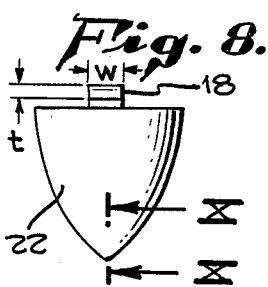
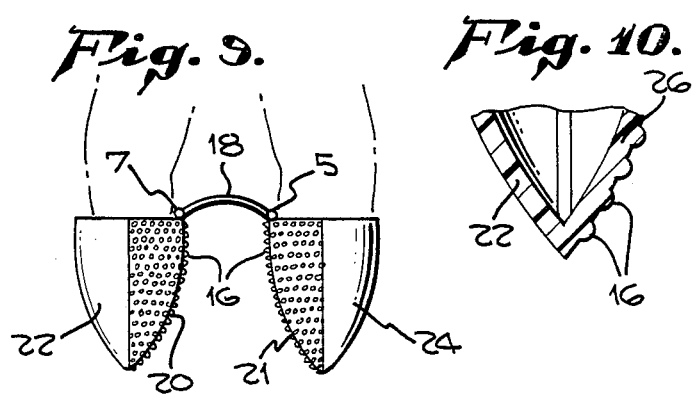
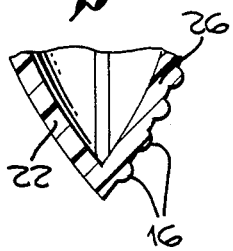

ORAL HYGIENE TONGUE HOLDER

This is a continuation of co-pending application Ser. No. 894,086 filed on Aug. 7, 1986, now abandoned which application is a continuation of the now-abandoned prior application Ser. No. 800,352, filed Nov. 20, 1985, which is in turn a continuation of the now-abandoned prior application Ser. No. 708,113, filed Mar. 5, 1985, which is in turn a continuation of the now-abandoned prior original application Ser. No. 357,198, filed Mar. 11, 1982.

FIELD OF THE INVENTION

This invention relates in general to apparatus and methods for restraining body organs and more particularly to apparatus and methods for grasping and restraining a tongue comfortably and without slippage while some operation is being performed inside the mouth.

BACKGROUND OF THE INVENTION

It is often necessary to restrain the movement of a tongue in order to perform some operation upon it or some other part of the mouth. For example, it is well-known that the tongue should be brushed contemporaneously with the brushing of teeth in order to thoroughly cleanse the mouth and to prevent accumulation of unhealthful deposits on the surface of the tongue.

After an eating process takes place, the tongue becomes coated with food particles which, in turn, turn into bacteria in the mouth. This bacteria is known to cause disease of the teeth, gums, and create halitosis. Even though teeth may be brushed and dental-flossed daily, the bacteria remains on the coated tongue. The invention of the tongue holder is necessary for better oral hygiene and for the prevention of many diseases stemming through the decayed teeth and gums. Today people are very conscious of their health and physical well being because of public exposure to government statistics on proper eating habits and exercise, and would welcome such a tool for the betterment of their health.

The tongue, however, is a slippery organ which is difficult to hold with the bare fingers, especially while withdrawing it from inside the mouth to its full length to facilitate performing an operation thereon such as brushing. There are no presently available devices which are adapted to comfortably restrain the tongue, while at the same time being easy to manipulate with the hand. The presently available clamping mechanisms may cause discomfort when applied to the tongue with the necessary force to hold it in place, are not easily held by a user, and are difficult to keep clean and sanitary. Gloves are relatively difficult to place over the hand, are relatively expensive, are difficult to keep clean, may not have suitable non-slip surfaces, or may not be impervious to moisture.

Accordingly, a principal object of the present invention is to provide a convenient and practical apparatus and method for gripping and restraining a tongue. Additional objects are that it be is easily attached to a user's finger and thumb, that it be small, simply constructed, inexpensive, and that it include a comfortable surface to be applied to the tongue, which securely restrains the tongue even in a fully extended position.

SUMMARY OF THE INVENTION

In a broad aspect of the invention, clasping means comprising upper and lower clasping members are provided for positioning above and below the tongue so that it will be securely and comfortably restrained. Attaching means secure the clasping members to a user's finger and thumb. An interconnecting means joins the two clasping members together in spaced relationship to one another allowing the clasping members to optimally contact the tongue when they are manipulated by the finger and thumb.

Additionally, in another aspect of the invention, gripping means which are impervious to moisture are provided for application to the tongue. These surfaces comfortably contact the upper and lower tongue surfaces to prevent slippage of the tongue without the necessity for applying excessive force.

In accordance with another important aspect of the invention, the interconnecting means are maintained in a predetermined spaced relationship to one another so that the tongue-holding members may easily be slipped over the user's finger and thumb, and further so that the tongue-holding members are maintained in this predetermined spaced relationship while being used. Lateral movement of one tongue-holding member relative to the other is simultaneously restricted so that the user need not be unduly concerned with maintaining the surfaces in an optimum relationship with one another, because they will be so maintained by the structure itself. This results in a positive yet comfortable contact with the tongue.

In accordance with other aspects of the invention, the attaching means are comprised of loops or an integral finger cover for securely attaching the apparatus to the user's finger and thumb in a simple and straightforward manner so that the device may quickly and easily be attached or removed.

In another aspect of the invention, the gripping means comprise non-slip surfaces to engage the tongue in a manner to prevent slippage. These non-slip surfaces may include a plurality of projections extending outwardly from the surface of the gripping means, or may have a textured surface to prevent unwanted disengagement of the tongue and may, for example, be molded out of an elastomeric compound.

BRIEF DESCRIPTION OF THE DRAWINGS

FIG. 1 is a perspective view illustrating a preferred embodiment of the present invention.

FIG. 2 is a top view of the apparatus depicted in FIG. 1.

FIG. 3 is an end view of the apparatus depicted in FIG. 1.

FIG. 4 is a side view of the apparatus depicted in FIG. 1 showing it attached to a user's index finger and thumb which are shown in phantom lines.

FIG. 5 is a section view taken along the plane V—V in FIG. 3.

FIg. 6 is a perspective view of an alternative embodiment of the present apparatus.

FIG. 7 is a top view of the apparatus depicted in FIG. 6.

FIG. 8 is an end view of the apparatus depicted in FIG. 6.

FIG. 9 is a side view of the apparatus depicted in FIG. 6, shown attached to a user's index finger and thumb shown in phantom lines.

FIG. 10 is a sectional view taken along the plane X—X in FIG. 8.

FIG. 11 is a partial cross-sectional view similar to FIG. 5 showing an alternate embodiment of the gripping means.

DETAILED DESCRIPTION

A preferred embodiment of a tongue holder for restraining a tongue with the user's finger and thumb is depicted in FIGS. 1–5 of the drawings. In FIG. 1, the preferred embodiment of the invention is depicted in perspective view. A clasping means including a first clasping member 2 is shown standing in parallel spaced relationship to second clasping member 4. The two clasping members are maintained in this relationship to one another by interconnecting means 6, which in this embodiment is a flexible joining member comprising a link or hinge one end of which is attached to each of the two clasping members 2 and 4 at points 5 and 7 in any suitable fashion including bonding, pinning, or molding unitarily as part of the clasping members 2 and 4. Attaching means 8 and 10, which in the preferred embodiment are comprised of arcuate loops, are fastened to the periphery of each clasping member by any suitable fastening means including bonding or unitary molding integral with the clasping members 2 and 4. The attaching means 8 and 10 are preferrably constructed of a rigid or semi-rigid material such as a plastic polymer so that they will maintain their arcuate shape when the tongue holder is not attached to the user's finger and thumb. This allows for quick and easy insertion and removal of the finger and thumb. One important advantage of using loops as the attaching means 8 and 10 is that a user with long fingernails may easily and comfortably attach and use the tongue holder.

Gripping means 12 and 13 are provided for engaging the tongue and preventing slippage while the tongue holder is in use, and in the preferred embodiment are a plurality of bristle like projections. In FIG. 5 which is a section through clasping member 2 and which shows a typical view of the gripping means at any point on its surface, the projections are clearly shown. The projections 14 may be of varying length, thickness and cross-sectional configuration, depending largely upon the manufacturing technique chosen. For example, the projections 14 may be conical (See FIG. 11), wherein the height of each cone is nearly equal to the diameter of its base, facilitating manufacture by an injection molding process. The projections 14 may be attached to the clasping members 2 and 4 by any suitable means including bonding. However, they may easily be molded integral to clasping members 2 or 4, and such a construction is shown in FIG. 5. The material used for the clasping members 2 and 4 and for the projections 14 may be any suitable plastic or rubber compound. The gripping means 12 and 13 are not limited to projections 14, but may be any suitable non-slip surface which is impervious to moisture.

One such alternative surface is depicted in FIGS. 6 through 10. In this alternative embodiment, gripping means 20 and 21 include a textured surface 16 attached to clasping member 26 and 27. The configuration of the texture is not critical and may be comprised of either bumps as depicted in FIG. 10, or waves, ridges, or other suitable design which has the effect of preventing slippage of the tongue when engaged by the tongue holder. This surface may be constructed of an elastomeric compound which is flexible and easily attached to the contour of the clasping member 26. Textured surface 16 may be mounted to the clasping members 26 and 27 by any suitable method including bonding, or may be molded directly as part of the clasping members 26 and 27.

The gripping means 12 and 13 of the embodiment depicted in FIGS. 1 through 5, and the gripping means 20 and 21 depicted in FIGS. 6 through 10 are interchangeable with each other and with other surfaces which will serve the same function, such as roughened, chemically impregnated paper.

FIG. 2 is a top view of the tongue holder depicted in FIG. 1. In this view, the arcuate attaching means 8 and 10 can be clearly seen. The curved shape facilitates a comfortable attachment of the tongue holder to the user's finger and thumb. The attaching means 8 and 10 may be constructed of an elastic material which is stretched when the finger and thumb are inserted to provide a snug, secure fit while being used. The gripping means are shown as 12 and 13.

The interconnecting means 6, which was described earlier, is represented in detail in FIG. 3. The interconnecting means 6 is shown to have a greater width "w" than thickness "t". This allows the interconnecting means 6 to have greater elasticity in the direction of opposing movement, which allows the clasping members 2 and 4 to be moved toward and apart from one another with relative ease, while at the same time preventing excessive lateral movement of clasping member 2 relative to clasping member 4. This insures tht the gripping means 12 and 13 will make an optimum contact with the upper and lower surfaces of the tongue, and also holds the two clasping members 2 and 4 in a predetermined spaced relationship relative to one another when the tongue holder is not in use, to facilitate easy insertion of the thumb and index finger by the user. The dimensions "w" and "t" may be altered relative to one another depending upon the material chosen for the interconnecting means 6, in order to accomplish the objectives discussed above. It is also possible to construct interconnecting means 6 out of a composite material or in multiple layers wherein one or more layers would have a significantly greater bending moment in one direction than the other to allow the clasping members 2 and 4 to be manipulated in the optimal manner described above.

The clasping members 2 and 4 may be sized as desired to accommodate various finger sizes. The shape depicted in FIG. 3 is circular because it is easy to construct, but it may also be any of a number of other suitable shapes such as an oval or square.

FIG. 4 depicts a forefinger and thumb shown in phantom lines in position to manipulate the tongue holder for engaging the tongue. As was stated before, the gripping means 12 and 13 may either be projections 14 as shown in FIG. 5, a surface 20, 21 as shown in FIGS. 6–10, or another suitable surface which will insure a non-slip engagement with the tongue to prevent slippage. The clasping members 2 and 4 are made of a material which is impervious to moisture so that the finger and thumb are kept dry while the tongue holder is in use.

An alternative embodiment of the present invention is shown in FIGS. 6–10. The interconnecting means 18 is constructed in the same manner as in the preferred embodiment, having a larger width "w" than thickness "t". It holds gripping means 20 in a predetermined spaced relationship to gripping means 21 to allow for easy insertion of the finger and thumb, and to insure an optimal contact with the tongue. The major difference between this embodiment and the previous one, is that the attaching means 22 and 24, rather than being comprised of one or more arcuate loops attached to the periphery of the clasping members 26 and 27, are instead comprised of finger covers integral with the clasping members 26 and 27 to form pockets into which the finger and thumb are inserted. One advantage to this type of construction is that the thumb and finger are better protected and kept drier when the tongue holder is being used.

The clasping members 26 and 27 are shown to have a curved shape similar to the shape of the attaching means 22 and 24 (FIG. 7). This again allows for comfortable use and may also simplify construction of the tongue holder. As in the preferred embodiment, the attaching means 22 and 24 are secured to the clasping members 26 and 27 by any suitable means such as bonding or unitary molding wherein the attaching means 22 and 24 are made integral with clasping members 26 and 27, as by injection molding.

As before, interconnecting means 18 has a larger width "w" than thickness "t" to allow for the freest movement in one plane only as described previously.

FIG. 9 shows this embodiment as attached to a finger and thumb shown in phantom lines. Because the gripping means 20 and 21 are curved in three dimensions, contact with the tongue is assured even if little care is taken by the user in attaching the tongue holder to the finger and thumb and in manipulating it around the tongue.

It is to be understood that the disclosed apparatus is merely illustrative of the principles of the present invention which could be implemented by other types of structures constructed of different materials such as metals. Accordingly, the scope of the present invention is to be determined in accordance with the appended claims.

What is claimed is:

1. A tongue holding aid for improving the grip maintainable by a user's thumb and finger on a tongue, said tongue holding aid being formed of a flexible material and comprising:
    first and second clasping members, each of said clasping members comprising a circular disk having oppositely disposed first and second circular sides,
    finger attaching means on the first side of each circular disk for removably attaching said clasping member to one of the thumb and finger of the user, said finger attaching means comprising a loop affixed to each circular disk at diametrically opposite attachment points adjacent the periphery thereof, said loop having a substantially semicircular arcuate shape which forms an opening for receiving one of the thumb and finger of the user;
    gripping means on said second side of each circular disk for providing a non-slip grip on a surface of the tongue; and
    flexible interconnecting means for interconnecting said first and second clasping members in a spaced apart relationship, said flexible interconnecting means being affixed to each circular disc adjacent the periphery thereof at a point angularly spaced from the attachment points of the loop associated therewith, the clasping members, finger attaching means, gripping means and flexible interconnecting means comprising a unitary structure molded in one piece of a flexible elastomeric material.

2. The tongue holding aid of claim 1 wherein the angular spacing of the affixation point of the flexible interconnecting means from the attachment points of the loop to each circular disk is about 90°.

3. The tongue holding aid of claim 1 wherein said gripping means comprise a plurality of substantially cylindrical projections extending perpendicularly from said second side of each circular disk.

4. The tongue holding aid of claim 1 wherein said elastomeric material is a plastic or rubber compound.

5. The tongue holding aid of claim 1 wherein the first and second circular sides of each circular disk are substantially planar and parallel to one another.

6. The tongue holding aid of claim 5 wherein said interconnecting means are affixed to the periphery of each circular disk at a location intermediate the first and second sides of each disk.

7. A tongue holding aid for improving the grip maintainable by a user's thumb and finger on a tongue, said tongue holding aid being formed of a flexible material and comprising:
    first and second clasping means, each of said clasping means comprising a member having a periphery and oppositely disposed first and second sides;
    finger attaching means on the first side of each member for removably attaching said clasping means to one of the thumb and finger of the user, said finger attaching means comprising a loop affixed to each member at opposite attachment points adjacent the periphery thereof, said loop having a shape which forms an opening for receiving one of the thumb and finger of the user;
    gripping means on said second side of each member for providing a non-slip grip on a surface of the tongue, said gripping means comprising a plurality of substantially cylindrical projections extending perpendicularly from said second side of said member;
    flexible interconnecting means for interconnecting said first and second clasping means in a spaced apart relationship, said flexible interconnecting means being affixed to each member adjacent the periphery thereof at a point angularly spaced from the attachment points of the loop associated therewith.

8. The tongue holding aid of claim 7, wherein the clasping means, finger attaching means, gripping means and flexible interconnecting means comprise a unitary structure molded in one piece of a flexible elastomeric material.

9. The tongue holding aid of claim 8, wherein said members of said clasping means comprise a circular disk.

10. The tongue holding aid of claim 9, wherein said first and second sides are circular and substantially planar and parallel to one another.

11. The tongue holding aid of claim 10, wherein said loop has a substantially semicircular arcuate shape.

12. A tongue holding aid for improving the grip maintainable by a user's thumb and finger on a tongue, said tongue holding aid being formed of a flexible material and comprising:
    first and second clasping means, each of said clasping means comprising a member having a periphery and oppositely disposed first and second sides;
    finger attaching means on the first side of each member for removably attaching said clasping means to one of the thumb and finger of the user, said finger attaching means comprising a loop affixed to each member at opposite attachment points adjacent the periphery thereof, said loop having a shape which forms an opening for receiving one of the thumb and finger of the user;

gripping means on said second side of each member for providing a non-slip grip on a surface of the tongue;

flexible interconnecting means for interconnecting said first and second clasping means in a spaced apart relationship, said flexible interconnecting means being affixed to each member adjacent the periphery thereof at a point angularly spaced from the attachment points of the loop associated therewith.

13. The tongue holding aid of claim 12 wherein said gripping means comprises a plurality of substantially cylindrical projections extending perpendicularly from said second side of said member.

14. The tongue holding aid of claim 13, wherein the clasping means, finger attaching means, gripping means and flexible interconnecting means comprise a unitary structure molded in one piece of a flexible elastomeric material.

15. The tongue holding aid of claim 14, wherein said members of said clasping means comprise a circular disk.

16. The tongue holding aid of claim 15, wherein said first and second sides are circular and substantially planar and parallel to one another.

17. The tongue holding aid of claim 16, wherein said loop has a substantially semicircular arcurate shape.

* * * * *